United States Patent
Song et al.

(10) Patent No.: US 8,901,366 B2
(45) Date of Patent: Dec. 2, 2014

(54) URINE VOLUME HYDRATION TEST DEVICES

(75) Inventors: Xuedong Song, Roswell, GA (US); RameshBabu Boga, Alpharetta, GA (US); Ning Wei, Roswell, GA (US)

(73) Assignee: Kimberly Clark Worldwide, Inc., Neenah, WI (US)

( * ) Notice: Subject to any disclaimer, the term of this patent is extended or adjusted under 35 U.S.C. 154(b) by 1991 days.

(21) Appl. No.: 11/956,415

(22) Filed: Dec. 14, 2007

(65) Prior Publication Data
US 2009/0157023 A1    Jun. 18, 2009

(51) Int. Cl.
| A61F 13/15 | (2006.01) |
| G01N 21/80 | (2006.01) |
| A61F 13/84 | (2006.01) |
| G01N 33/52 | (2006.01) |
| G01N 33/84 | (2006.01) |
| A61F 13/42 | (2006.01) |

(52) U.S. Cl.
CPC ........... *G01N 21/80* (2013.01); *A61F 13/84* (2013.01); *A61F 2013/8473* (2013.01); *A61F 2013/427* (2013.01); *A61F 13/42* (2013.01); *G01N 33/521* (2013.01); *G01N 33/84* (2013.01)
USPC ........... 604/361; 600/361; 600/362; 436/169

(58) Field of Classification Search
CPC ... A61F 13/42; A61F 13/84; A61F 2103/427; A61F 2103/8473; A61F 2103/8488
USPC ........... 604/361; 600/309, 361–362; 436/514, 436/161–163, 169
See application file for complete search history.

(56) References Cited

U.S. PATENT DOCUMENTS

| 4,704,116 A | 11/1987 | Enloe |
| 5,075,077 A | 12/1991 | Durley, III et al. |
| 5,192,606 A | 3/1993 | Proxmire et al. |
| 5,252,459 A | 10/1993 | Tarcha et al. |
| 5,354,289 A * | 10/1994 | Mitchell et al. ............... 604/361 |
| H1376 H * | 11/1994 | Osborn et al. |
| 5,399,219 A | 3/1995 | Roessler et al. |
| 5,486,166 A | 1/1996 | Bishop et al. |
| 5,490,846 A | 2/1996 | Ellis et al. |
| 5,540,796 A | 7/1996 | Fries |
| 5,595,618 A | 1/1997 | Fries |
| 5,647,863 A * | 7/1997 | Hammons et al. ............ 604/378 |

(Continued)

FOREIGN PATENT DOCUMENTS

| KR | 10-1996-0040334 A | 12/1996 |
| WO | WO 9516425 | 6/2005 |
| WO | WO 2006/118647 A1 | 11/2006 |

OTHER PUBLICATIONS (PCT/IB2008/053658) International Search Report—3 pages.

*Primary Examiner* — Lynne Anderson
(74) *Attorney, Agent, or Firm* — Dority & Manning, P.A.

(57) ABSTRACT

In accordance with one embodiment of the present disclosure, a method for quantitatively or semi-quantitatively determining the volume of a test sample of urine is provided. The method includes contacting the test sample with a fluidic medium of a lateral flow device having a volume indicator disposed thereon and determining the volume of urine in the test sample based on the distance traveled by the volume indicator along the fluidic medium, the distance traveled by the volume indicator corresponding to the volume of urine in the test sample.

25 Claims, 4 Drawing Sheets

(56) References Cited

U.S. PATENT DOCUMENTS

| | | |
|---|---|---|
| 5,670,381 A | 9/1997 | Jou et al. |
| 5,702,377 A | 12/1997 | Collier, IV et al. |
| 5,931,823 A | 8/1999 | Stokes et al. |
| 6,060,638 A | 5/2000 | Paul et al. |
| 6,150,002 A | 11/2000 | Varona |
| 6,663,611 B2 | 12/2003 | Blaney et al. |
| 2003/0158530 A1* | 8/2003 | Diehl et al. ............... 604/361 |
| 2003/0164136 A1* | 9/2003 | Klofta et al. ............... 116/206 |
| 2004/0102750 A1 | 5/2004 | Jameson |
| 2004/0133090 A1* | 7/2004 | Dostoinov et al. ............ 600/362 |
| 2005/0054255 A1 | 3/2005 | Morman et al. |
| 2005/0059941 A1 | 3/2005 | Baldwin et al. |
| 2006/0229578 A1* | 10/2006 | Roe et al. ............... 604/361 |
| 2007/0185467 A1* | 8/2007 | Klofta et al. ............... 604/361 |
| 2008/0147031 A1* | 6/2008 | Long et al. ............... 604/361 |
| 2009/0326494 A1* | 12/2009 | Uchida et al. ............... 604/361 |

\* cited by examiner

URINE VOLUME HYDRATION TEST DEVICES

BACKGROUND

Dehydration is the abnormal depletion of bodily fluids and can have very serious consequences if not cared for properly. Dehydration can be of particular concern for the elderly and babies. Determination of urine volume can aid in determining hydration status in individuals.

Specifically, total body water is regulated within approximately about ±0.2% of body weight each day, and it comprises approximately about 63% of the entire body mass. The water balance is achieved and maintained by matching the input and output of water from the body, and a water imbalance, as detected from urine volume, can be linked to dehydration or hypohydration. Loss of body water in amounts of less than from about 2-3% body mass have been associated with reduced heat dissipation, loss of cardiovascular function, and decreased physical stamina.

However, conventional reagent strips do not have a mechanism by which urine volume can be determined in an effective manner that is not cost prohibitive.

Thus, a need exists for a testing device that can signal urine volume in a cost-effective way. In addition, a need exists for a testing device that can signal urine volume to more accurately detect dehydration in individuals. An absorbent article that incorporates such a device would be particularly beneficial.

SUMMARY

In accordance with one embodiment of the present disclosure, a method for quantitatively or semi-quantitatively determining the volume of a test sample of urine is provided. The method includes contacting the test sample with a fluidic medium of a lateral flow device having a volume indicator disposed thereon and determining the volume of urine in the test sample based on the distance traveled by the volume indicator along the fluidic medium, the distance traveled by the volume indicator corresponding to the volume of urine in the test sample.

In another embodiment of the present disclosure, a method for quantitatively or semi-quantitatively determining the volume and ionic strength of a test sample of urine is described. The method includes contacting the test sample with a fluidic medium of a lateral flow device, the fluidic medium having a volume indicator, a polyelectrolyte, and a pH indicator disposed thereon. The polyelectrolyte is capable of an ion-exchange with the urine so as to add hydrogen ions into the urine and the pH indicator capable of producing a signal corresponding to the hydrogen ion concentration in the urine. The volume of urine in the test sample is determined based on the distance traveled by the volume indicator along the fluidic medium, the distance traveled by the volume indicator corresponding to the volume of urine in the test sample. The ionic strength of the urine is determined based on the signal produced by the pH indicator.

In still another embodiment of the present disclosure, a lateral flow assay device for determining the volume and ionic strength of a test sample of urine is described. The, the device includes a chromatographic medium having a volume indicator, a polyelectrolyte, and a pH indicator disposed thereon.

In yet another embodiment of the present disclosure, an absorbent article capable of determining the ionic strength of urine is described.

Other features and aspects of the present disclosure are discussed in greater detail below.

BRIEF DESCRIPTION OF THE DRAWINGS

A full and enabling disclosure, including the best mode thereof, directed to one of ordinary skill in the art, is set forth more particularly in the remainder of the specification, which makes reference to the appended figure in which.

Figure 1:
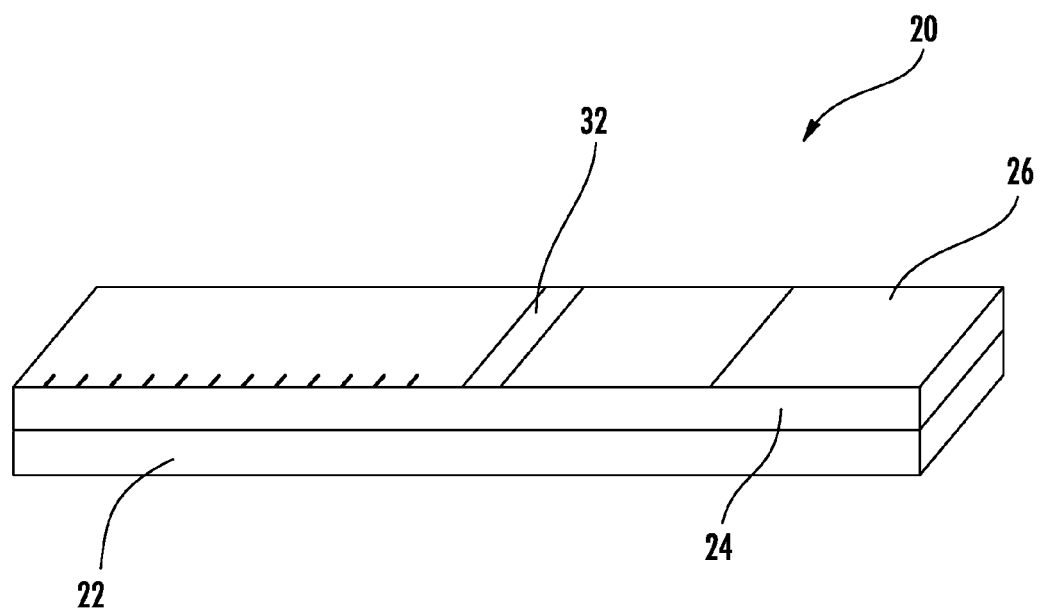
FIG. 1 shows a perspective view of one embodiment of a device that can be used in the present disclosure.

Repeat use of reference characters in the present specification and drawings is intended to represent same or analogous features or elements of the disclosure.

DETAILED DESCRIPTION

Reference now will be made in detail to various embodiments of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment, can be used on another embodiment to yield a still further embodiment. Thus, it is intended that the present disclosure covers such modifications and variations as come within the scope of the appended claims and their equivalents.

As described above, it is well known to utilize urine specific gravity (USG) to indicate the presence or degree of dehydration in human subjects. Since the specific gravity of urine is correlated to the ionic strength of urine, measurements of urine ionic strength can be used to estimate specific gravity in devices screening for the presence or severity of dehydration.

However, conventional test strips do not have a mechanism for indicating urine volume. In that regard, the present disclosure is generally directed to a lateral flow assay device that can determine the volume of a test sample of urine. The device includes a volume indicator that is capable of traveling a distance along the device that corresponds to the volume of urine in the test sample.

The devices described herein provide a simple, user-friendly, cost-effective approach for rapid measurement of hydration status. Additionally, the devices described herein can be incorporated into absorbent articles such as diapers and incontinent pads.

Referring to FIG. 1, one embodiment of a lateral flow device 20 that can be formed according to the present disclosure will now be described in more detail. As shown, the device 20 contains a chromatographic medium 24 optionally supported by a rigid support material 22. In general, the chromatographic medium 24 can be made from any of a variety of materials through which the urine is capable of passing. For example, the chromatographic medium 24 can be a porous membrane formed from synthetic or naturally occurring materials, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth.

The size and shape of the chromatographic medium 24 can generally vary as is readily recognized by those skilled in the art. For instance, a porous membrane strip can have a length of from about 10 to about 100 millimeters, in some embodiments from about 20 to about 80 millimeters, and in some embodiments, from about 40 to about 60 millimeters. The length should be sufficient so that the volume indicator (described further hereafter) can travel a sufficient distance to correlate with the volume of the urine sample.

The width of the membrane strip can also range from about 0.5 to about 20 millimeters, in some embodiments from about 1 to about 15 millimeters, and in some embodiments, from about 2 to about 10 millimeters. The thickness of the membrane strip can be less than about 500 micrometers, in some embodiments less than about 250 micrometers, and in some embodiments, less than about 150 micrometers.

As stated above, the support 22 carries the chromatographic medium 24. For example, the support 22 can be positioned directly adjacent to the chromatographic medium 24 as shown in FIG. 1, or one or more intervening layers can be positioned between the chromatographic medium 24 and the support 22. Regardless, the support 22 can generally be formed from any material able to carry the chromatographic medium 24. Also, it is generally desired that the support 22 is liquid-impermeable so that fluid flowing through the medium 24 does not leak through the support 22. Examples of suitable materials for the support include, but are not limited to, glass; polymeric materials, such as polystyrene, polypropylene, polyester (e.g., Mylar® film), polybutadiene, polyvinylchloride, polyamide, polycarbonate, epoxides, methacrylates, and polymelamine; and so forth. To provide a sufficient structural backing for the chromatographic medium 24, the support 22 is generally selected to have a certain minimum thickness. Thus, for example, the support 22 can have a thickness that ranges from about 100 to about 5,000 micrometers, in some embodiments from about 150 to about 2,000 micrometers, and in some embodiments, from about 250 to about 1,000 micrometers. For instance, one suitable membrane strip having a thickness of about 125 micrometers can be obtained from Millipore Corp. of Bedford, Mass. under the name "SHF180UB25."

As is well known the art, the chromatographic medium 24 can be cast onto the support 22, wherein the resulting laminate can be die-cut to the desired size and shape. Alternatively, the chromatographic medium 24 can simply be laminated to the support 22 with, for example, an adhesive. In some embodiments, a nitrocellulose or nylon porous membrane is adhered to a Mylar® film. An adhesive is used to bind the porous membrane to the Mylar® film, such as a pressure-sensitive adhesive. Laminate structures of this type are believed to be commercially available from Millipore Corp. of Bedford, Mass. Still other examples of suitable laminate device structures are described in U.S. Pat. No. 5,075,077 to Durley, III, et al., which is incorporated herein in its entirety by reference thereto for all purposes.

To initiate the measurement of the volume of urine, a user can directly apply the test sample to a portion of the chromatographic medium 24 through which it can then travel in the direction illustrated by arrow "L" in FIG. 1. Alternatively, the test sample can first be applied to a sample application zone 26 that is in fluid communication with the chromatographic medium 24. As shown in FIG. 1, the sample application zone 26 can be formed on the medium 24. The sample application zone 26 can also be formed by a separate material, such as a pad. Some suitable materials that can be used to form such sample pads include, but are not limited to, nitrocellulose, cellulose, porous polyethylene pads, and glass fiber filter paper. If desired, the sample application zone 26 can also contain one or more pretreatment reagents, either diffusively or non-diffusively attached thereto.

To facilitate measurement of the volume of the urine in the test sample, a volume indicator is positioned on the device. The volume indicator 28 can be disposed in the sample application zone 26. In this manner, the urine sample is capable of mixing with the volume indicator upon application. Alternatively, the volume indicator 28 can be disposed downstream from the sample application zone 26.

Figure 2:
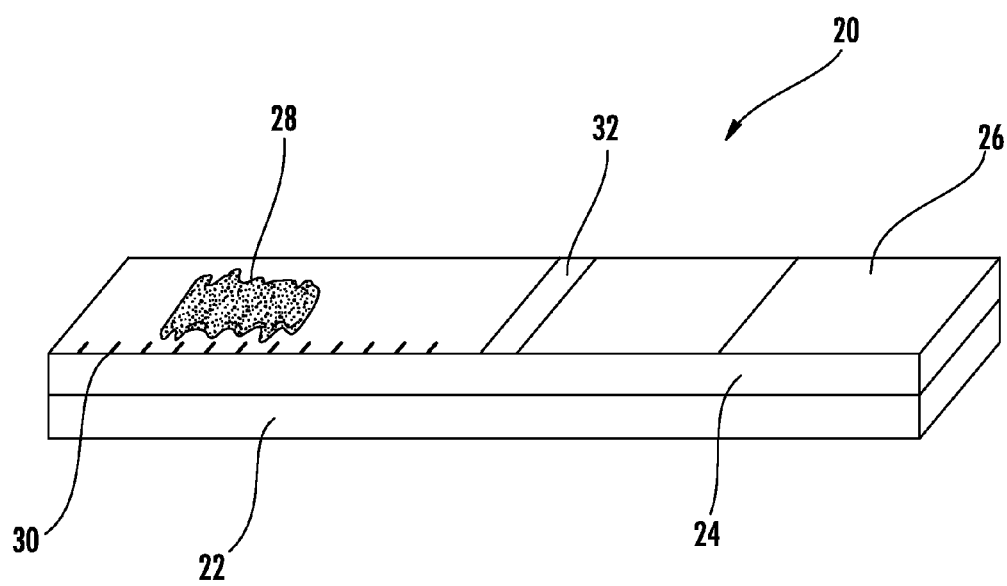
FIG. 2 shows a perspective view of one embodiment of a device that can be used in the present disclosure.

Referring to FIG. 2, the volume indicator 28 is configured to flow through the chromatographic medium 24 upon contact with a volume of the urine test sample. It has been determined that the migration of the volume indicator 28 along the chromatographic medium 24 correlates with the volume of liquid in the urine sample. In this manner, depending on the particular material utilized to form the chromatographic medium 24 as well as the material utilized for the volume indicator, one can determine the volume of liquid in the urine sample by determining how far the volume indicator travels. The volume indicator 28 can be observed, either visually or with an instrument, along the entirety of the chromatographic medium 24.

Depending on the material chosen for the chromatographic medium 24, including the size and shape of such material, the volume of liquid in the urine sample can be determined based on how far the volume indicator 28 travels along such material. Similarly, depending on the particular volume indicator 28 chosen, including the size and shape of such volume indicator 28, the volume of liquid in the urine sample can be determined based on how far the volume indicator 28 travels. Such determinations can be made before the device is offered to consumers so that information can be provided with the device that correlates the distance traveled by the volume indicator 28 along the chromatographic medium 24 with a volume of urine.

For instance, in certain embodiments, markings 30 can be made along the length of the chromatographic medium 24 that can assist in approximation of the volume of the urine sample based on the distance traveled by the volume indicator 28. In still other embodiments, sensors can be utilized that determine the distance traveled by the volume indicator to provide the user with an indication of the volume of the urine sample.

Many suitable volume indicators can be utilized that flow through the chromatographic medium 24 upon contact with a volume of the urine test sample. These volume indicators can then be observed, either visually or with an instrument, along the chromatographic medium 24. The volume indicators can generally be detectable substances, such as luminescent compounds (e.g., fluorescent, phosphorescent, etc.); radioactive compounds; visual compounds (e.g., colored dye or metallic substance, such as gold); liposomes or other vesicles containing signal-producing substances; enzymes and/or substrates, and combinations thereof. Other suitable volume indicators are described in U.S. Pat. No. 5,670,381 to Jou, et al. and U.S. Pat. No. 5,252,459 to Tarcha, et al., which are incorporated herein in their entirety by reference thereto for all purposes. If desired, the volume indicators can be disposed on particles such as described above. For example, latex particles may be utilized that are labeled with a fluorescent or colored dye. Commercially available examples of suitable fluorescent particles include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc. In addition, commercially available examples of suitable colored, latex microparticles include carboxylated latex beads sold by Bang's Laboratory, Inc.

One particular embodiment of a method for detecting the volume of urine using the device 20 of FIG. 1 will now be described in more detail. Initially, a urine test sample is applied to the sample application zone 26 and travels in the direction "L" along the chromatographic medium 24. The distance the urine travels is dictated in large part by the amount of urine in the test sample. However, the material selected for the chromatographic medium 24 can also affect the distance traveled by the urine. It has been determined that the migration of the volume indicator 28 along the chromatographic medium 24 correlates with the volume of liquid in the urine sample. In this manner, depending on the particular material utilized to form the chromatographic medium 24 as well as the material utilized for the volume indicator, one can determine the volume of liquid in the urine sample by determining how far the volume indicator travels. The volume indicator 28 can be observed, either visually or with an instrument, along the entirety of the chromatographic medium 24.

Generally speaking, qualitative, quantitative, or semi-quantitative determination of the volume of urine can be achieved in accordance with the present disclosure. For example, as stated above, the volume of urine can be quantitatively or semi-quantitatively determined by using the distance traveled by the volume indicator 28 along the chromatographic medium 24. The ability to utilize the distance traveled by the volume indicator 28 to determine volume of urine is illustrated graphically in FIG. 4. It should be understood that the volume of urine correlated to the distance traveled does not necessarily have to exactly follow the illustrated relationship, and that this relationship is given for exemplary purposes only.

Figure 3:
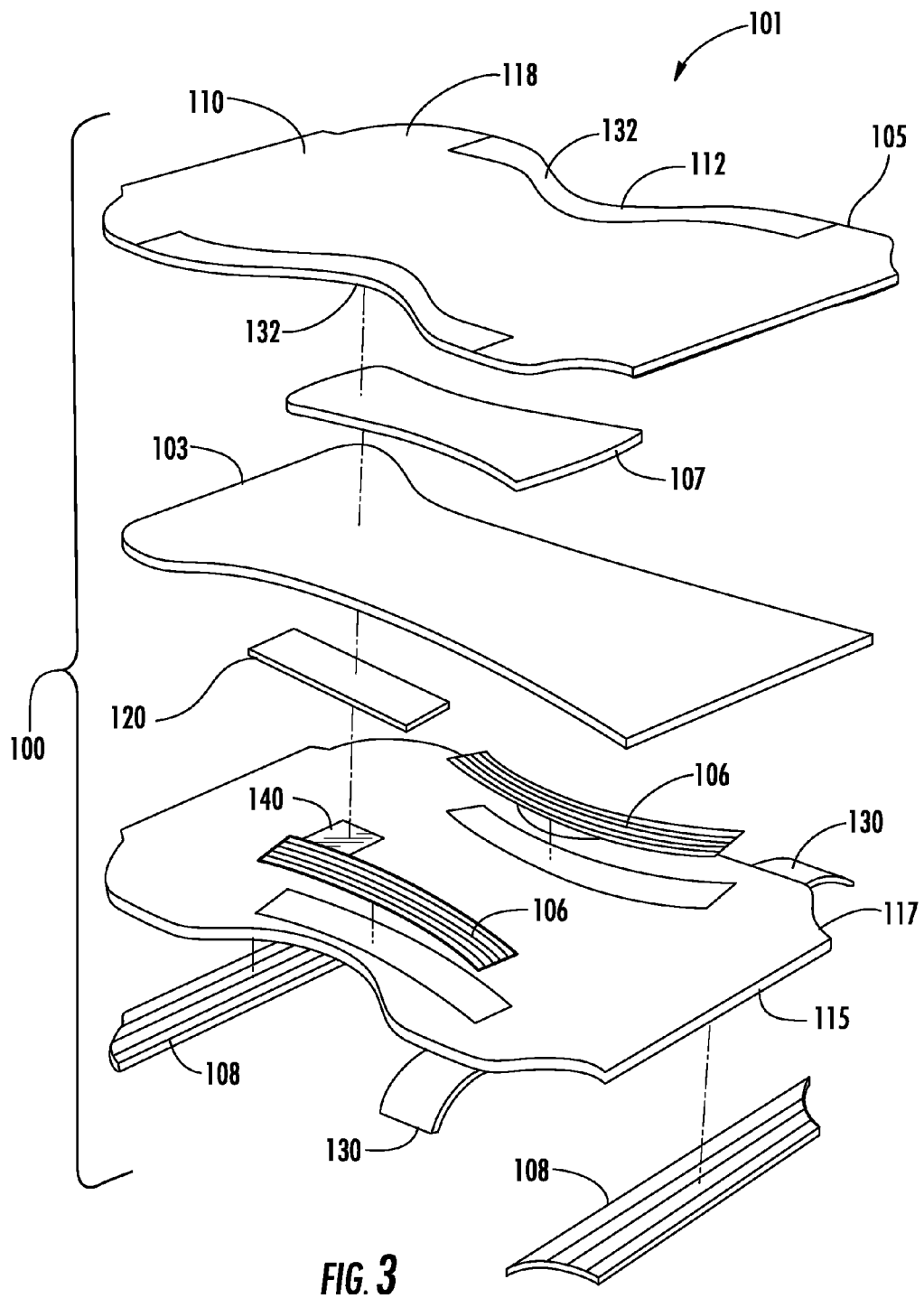
FIG. 3 shows a graph that correlates the volume of liquid in a sample with the migration of an indicator.

In this regard, FIG. 3 shows the relationship between the volume indicator 28 migration and volume of liquid. As shown, as volume indicator 28 migration increases, the volume of liquid in the sample also increases. Consequently, volume indicator migration bears an almost linear relationship with volume of liquid in the sample. Thus, such a graph can be used to accurately convert the measured and normalized indicator migration to an actual sample volume.

In certain embodiments, the device is also capable of determining the ionic strength of urine. The volume and ionic strength of urine are two factors that can provide information with respect to hydration status of an individual. In this manner, hydration status can be determined through urine utilizing two independent test criteria.

With reference to FIG. 1, to facilitate measurement of the ionic strength of urine, a polyelectrolyte is disposed on the chromatographic medium 24. In certain embodiments, the polyelectrolyte can be disposed in an ionic strength indication zone 32. The polyelectrolyte can be disposed downstream from the sample application zone 26. In this manner, the urine sample is capable of mixing with the polyelectrolyte upon application. Alternatively, the polyelectrolyte can be positioned upstream from the sample application zone 26. For instance, a diluent can be employed to induce mixing between the polyelectrolyte and test sample.

Ions present in urine induce an ion-exchange with the polyelectrolyte, so as to add or reduce the number of hydrogen ions in the urine. In this regard, a suitable polyelectrolyte can include a polymeric acid or a polymeric base, particularly weak polymeric acids and weak polymeric bases. Weak polymeric acids or bases change their apparent association/dissociation constants with the change of ion strength of their environments. For instance, when cation concentration increases, the dissociation constant of a carboxylic acid-based weak acid increases to release more protons to increase the acidity of the solution.

The selection of buffer components can be important for the measurement sensitivity and color change threshold of the device. In certain embodiments, the buffer system is preferably a partially neutralized weak polymeric acids or a partially neutralized weak polymeric base. In this regard, the apparent association constants or dissociation constants of the acids or bases utilized should be sufficiently sensitive to ion strength. There are a number suitable weak polymeric acids and bases that can be utilized with the present disclosure. For example, useful weak polymeric acids can include poly(acrylic acid), poly(maleic acid), maleic acid vinyl methyl ether copolymer, poly(methacrylic acid), styrenemaleic acid copolymer, and maleic anhydride/methylvinylether copolymer. Useful weak polymeric bases can include poly(vinylamine) and poly(4-vinylpyridine). However, it should be understood that any suitable polyelectrolyte is contemplated by the present disclosure.

In certain embodiments, polymeric acids or bases can be neutralized at least 50% to make an effective sensitive buffer. The initial pH of the buffer can normally be adjusted to a certain range so that the threshold color changes of the specific gravity can be tailored to some degree. For example, the threshold detection of USG is slightly higher when the initial buffer pH is higher. However, the adjustments can be limited by the intrinsic association/dissociation constants of the acids or bases utilized. The threshold of color transition can also be adjusted by using different buffer components. For instance, the threshold color change occurs around 1.020 of USG for poly(vinyl chloride-co-vinyl acetate-co-maleic acid while the threshold transition point is around 1.010 for poly(acrylic acid) when both buffers have the initial pH of 7.95.

Referring again to FIG. 1, the lateral flow device 20 also includes a pH indicator disposed on the chromatographic medium 24. In certain embodiments, the pH indicator can be disposed in an ionic strength indication zone 32. The pH indicator can be applied directly to the medium 24 or first formed into a solution prior to application. Various solvents can be utilized to form the solution, such as, but not limited to, acetonitrile, dimethylsulfoxide (DMSO), ethyl alcohol, dimethylformamide (DMF), and other polar organic solvents. The amount of the pH indicator in the solution can range from about 0.001 to about 100 milligrams per milliliter of solvent, and in some embodiments, from about 0.1 to about 10 milligrams per milliliter of solvent. In one particular embodiment, the ionic strength indication zone 32 is defined by the chromatographic medium 24 and formed by coating a solution thereon using well-known techniques and then dried. The pH indicator concentration can be selectively controlled to provide the desired level of detection sensitivity.

It is important to select a pH indicator that has sensitivity towards the subtle pH change of the buffer caused by the ion strength of the urine. Since normal urine pH lies around neutral, the indicator is preferred to have a significant color transition around neutral pH. Examples of useful pH indicators can include Methyl violet, Malachite green, Thymol blue, Methyl yellow, Bromophenol blue, Congo red, Methyl orange, Bromocresol green, Methyl red, Litmus (Azolitmin), Bromocresol purple, Bromothymol blue, Methylene blue, Eriochrome Blue Black B, Erichrome Blue SE, Crystal violet, Phenol red, Neutral Red, Leucocrystal violet, Acid fuchsin, Phenolphthalein, Thymolphthalein, Alizarin Yellow R, Indigo carmine, and Universal indicators. However, any suitable pH indicator as would be known in the art is contemplated for use in the present disclosure.

In certain embodiments, the initial color of the pH indicator can be easily adjusted by including a pH adjuster, such as an acid, a buffer, a base or some combination thereof. The initial color is important to provide a sharp color contrast as large as possible. For instance, when bromothymol blue is used as an indicator, basic condition provides a vivid green color, which is clearly distinguishable from yellow color under slightly acidic condition.

In certain embodiments, the ionic strength of the urine sample can also be determined. In this regard, the urine test sample is applied to the sample application zone 26 and travels in the direction "L" along the chromatographic medium 24 to the ionic strength indication zone 32. At the ionic strength indication zone 32, the ions present in the urine sample induce an ion-exchange with the polyelectrolyte, thereby introducing hydrogen ions into the urine. The change in hydrogen ion concentration is detected by a pH indicator and the color or color intensity of the pH indicator can be determined, either visually or with instrumentation. If desired, the intensity of the color can be measured to quantitatively or semi-quantitatively determine the ionic strength of the urine and, in turn, the USG.

The present disclosure provides a relatively simple, compact and cost-efficient device for accurately detecting urine volume and/or USG. The test result can be visible so that it is readily observed by the person performing the test in a prompt manner and under test conditions conducive to highly reliable and consistent test results.

In accordance with the present disclosure, one or more devices described herein can also be integrated into an absorbent article. An "absorbent article" generally refers to any article capable of absorbing water or other fluids. Examples of some absorbent articles include, but are not limited to, personal care absorbent articles, such as diapers, training pants, absorbent underpants, incontinence articles, feminine hygiene products (e.g., sanitary napkins), swim wear, baby wipes, and so forth; medical absorbent articles, such as garments, fenestration materials, underzones, bedzones, bandages, absorbent drapes, and medical wipes; food service wipers; clothing articles; and so forth. Materials and processes suitable for forming such absorbent articles are well known to those skilled in the art. Typically, absorbent articles include a substantially liquid-impermeable layer (e.g., outer cover), a liquid-permeable layer (e.g., bodyside liner, surge layer, etc.), and an absorbent core.

Various embodiments of an absorbent article that can be formed according to the present invention will now be described in more detail. For purposes of illustration only, an absorbent article is shown in FIG. 3 as a diaper 101. In the illustrated embodiment, the diaper 101 is shown as having an hourglass shape in an unfastened configuration. However, other shapes can of course be utilized, such as a generally rectangular shape, T-shape, or I-shape. As shown, the diaper 101 includes a chassis formed by various components, including an outer cover 117, bodyside liner 105, absorbent core 103, and surge layer 107. It should be understood, however, that other layers can also be used in exemplary embodiments of the present invention. Likewise, one or more of the layers referred to in FIG. 3 can also be eliminated in certain exemplary embodiments of the present invention.

The bodyside liner 105 is generally employed to help isolate the wearer's skin from liquids held in the absorbent core 103. For example, the liner 105 presents a bodyfacing surface that is typically compliant, soft feeling, and non-irritating to the wearer's skin. Typically, the liner 105 is also less hydrophilic than the absorbent core 103 so that its surface remains relatively dry to the wearer. As indicated above, the liner 105 can be liquid-permeable to permit liquid to readily penetrate through its thickness. Exemplary liner constructions that contain a nonwoven web are described in U.S. Pat. Nos. 5,192,606 to Proxmire, et al.; 5,702,377 to Collier, IV, et al.; 5,931,823 to Stokes, et al.; 6,060,638 to Paul et al.; and 6,150,002 to Varona, as well as U.S. Patent Application Publication Nos. 2004/0102750 to Jameson; 2005/0054255 to Morman, et al.; and 2005/0059941 to Baldwin, et al., all of which are incorporated herein in their entirety by reference thereto for all purposes.

The diaper 101 can also include a surge layer 107 that helps to decelerate and diffuse surges or gushes of liquid that can be rapidly introduced into the absorbent core 103. Desirably, the surge layer 107 rapidly accepts and temporarily holds the liquid prior to releasing it into the storage or retention portions of the absorbent core 103. In the illustrated embodiment, for example, the surge layer 107 is interposed between an inwardly facing surface 116 of the bodyside liner 105 and the absorbent core 103. Alternatively, the surge layer 107 can be located on an outwardly facing surface 118 of the bodyside liner 105. The surge layer 107 is typically constructed from highly liquid-permeable materials. Examples of suitable surge layers are described in U.S. Pat. No. 5,486,166 to Ellis et al. and U.S. Pat. No. 5,490,846 to Ellis et al., which are incorporated herein in their entirety by reference thereto for all purposes.

The outer cover 117 is typically formed from a material that is substantially impermeable to liquids. For example, the outer cover 117 can be formed from a thin plastic film or other flexible liquid-impermeable material. In one embodiment, the outer cover 117 is formed from a polyethylene film having a thickness of from about 0.01 millimeter to about 0.05 millimeter. The film can be impermeable to liquids, but permeable to gases and water vapor (i.e., "breathable"). This permits vapors to escape from the absorbent core 103, but still prevents liquid exudates from passing through the outer cover 117. If a more cloth-like feeling is desired, the outer cover 117 can be formed from a polyolefin film laminated to a nonwoven web. For example, a stretch-thinned polypropylene film can be thermally laminated to a spunbond web of polypropylene fibers.

Besides the above-mentioned components, the diaper 101 can also contain various other components as is known in the art. For example, the diaper 101 can also contain a substantially hydrophilic tissue wrapsheet (not illustrated) that helps maintain the integrity of the fibrous structure of the absorbent core 103. The tissue wrapsheet is typically placed about the absorbent core 103 over at least the two major facing surfaces thereof, and composed of an absorbent cellulosic material, such as creped wadding or a high wet-strength tissue. The tissue wrapsheet can be configured to provide a wicking layer that helps to rapidly distribute liquid over the mass of absorbent fibers of the absorbent core 103. The wrapsheet material on one side of the absorbent fibrous mass can be bonded to the wrapsheet located on the opposite side of the fibrous mass to effectively entrap the absorbent core 103. Furthermore, the diaper 101 can also include a ventilation layer (not shown)

that is positioned between the absorbent core 103 and the outer cover 117. When utilized, the ventilation layer can help insulate the outer cover 117 from the absorbent core 103, thereby reducing dampness in the outer cover 117. Examples of such ventilation layers can include a nonwoven web laminated to a breathable film, such as described in U.S. Pat. No. 6,663,611 to Blaney, et al., which is incorporated herein in its entirety by reference thereto for all purposes.

In some embodiments, the diaper 101 can also include a pair of side panels (or ears) (not shown) that extend from the side edges 132 of the diaper 101 into one of the waist regions. The side panels can be integrally formed with a selected diaper component. For example, the side panels can be integrally formed with the outer cover 117 or from the material employed to provide the top surface. In alternative configurations, the side panels can be provided by members connected and assembled to the outer cover 117, the top surface, between the outer cover 117 and top surface, or in various other configurations. If desired, the side panels can be elasticized or otherwise rendered elastomeric by use of the elastic nonwoven composite of the present invention. Examples of absorbent articles that include elasticized side panels and selectively configured fastener tabs are described in PCT Patent Application WO 95/16425 to Roessler; U.S. Pat. No. 5,399,219 to Roessler et al.; U.S. Pat. No. 5,540,796 to Fries; and U.S. Pat. No. 5,595,618 to Fries, each of which is incorporated herein in its entirety by reference thereto for all purposes.

As representatively illustrated in FIG. 3, the diaper 101 can also include a pair of containment flaps 112 that are configured to provide a barrier and to contain the lateral flow of body exudates. The containment flaps 112 can be located along the laterally opposed side edges 132 of the bodyside liner 105 adjacent the side edges of the absorbent core 103. The containment flaps 112 can extend longitudinally along the entire length of the absorbent core 103, or can only extend partially along the length of the absorbent core 103. When the containment flaps 112 are shorter in length than the absorbent core 103, they can be selectively positioned anywhere along the side edges 132 of diaper 101 in a crotch region 110. In one embodiment, the containment flaps 112 extend along the entire length of the absorbent core 103 to better contain the body exudates. Such containment flaps 112 are generally well known to those skilled in the art. For example, suitable constructions and arrangements for the containment flaps 112 are described in U.S. Pat. No. 4,704,116 to Enloe, which is incorporated herein in its entirety by reference thereto for all purposes.

To provide improved fit and to help reduce leakage of body exudates, the diaper 101 can be elasticized with suitable elastic members, as further explained below. For example, as representatively illustrated in FIG. 3, the diaper 101 can include leg elastics 106 constructed to operably tension the side margins of the diaper 101 to provide elasticized leg bands which can closely fit around the legs of the wearer to reduce leakage and provide improved comfort and appearance. Waist elastics 108 can also be employed to elasticize the end margins of the diaper 101 to provide elasticized waistbands. The waist elastics 108 are configured to provide a resilient, comfortably close fit around the waist of the wearer.

The diaper 101 can also include one or more fasteners 130. For example, two flexible fasteners 130 are illustrated in FIG. 3 on opposite side edges of waist regions to create a waist opening and a pair of leg openings about the wearer. The shape of the fasteners 130 can generally vary, but can include, for instance, generally rectangular shapes, square shapes, circular shapes, triangular shapes, oval shapes, linear shapes, and so forth. The fasteners can include, for instance, a hook-and-loop material, buttons, pins, snaps, adhesive tape fasteners, cohesives, fabric-and-loop fasteners, etc. In one particular embodiment, each fastener 130 includes a separate piece of hook material affixed to the inside surface of a flexible backing.

The various regions and/or components of the diaper 101 can be assembled together using any known attachment mechanism, such as adhesive, ultrasonic, thermal bonds, etc. Suitable adhesives can include, for instance, hot melt adhesives, pressure-sensitive adhesives, and so forth. When utilized, the adhesive can be applied as a uniform layer, a patterned layer, a sprayed pattern, or any of separate lines, swirls or dots. In the illustrated embodiment, for example, the outer cover 117 and bodyside liner 105 are assembled to each other and to the absorbent core 103 using an adhesive. Alternatively, the absorbent core 103 can be connected to the outer cover 117 using conventional fasteners, such as buttons, hook and loop type fasteners, adhesive tape fasteners, and so forth. Similarly, other diaper components, such as the leg elastic members 106, waist elastic members 108 and fasteners 130, can also be assembled into the diaper 101 using any attachment mechanism.

Generally speaking, the devices of the present disclosure can be incorporated into the absorbent article in a variety of different orientations and configurations, so long as the device is capable of receiving urine and providing a signal to a user or caregiver of the USG. For example, the sampling zone and control zone can be visible to the user or caregiver so that a simple, accurate, and rapid indication of USG can be provided. The visibility of such layer(s) can be accomplished in a variety of ways. For example, in some embodiments, the absorbent article can include a transparent or translucent portion 140 (e.g., window, film, etc.) that allows the sampling zone and/or control zone to be readily viewed without removal of the absorbent article from the wearer and/or without disassembly of the absorbent article. In other embodiments, the sampling zone and/or control zone can extend through a hole or aperture in the absorbent article for observation. In still other embodiments, the sampling zone and/or control zone can simply be positioned on a surface of the absorbent article for observation.

Regardless of the particular manner in which it is integrated, urine can be directly discharged to a portion of the sampling zone, a liquid permeable cover or other material surrounding assay device 120, or can be discharged onto a component of the absorbent article into which the assay device 120 has been integrated.

After a sufficient reaction time, the intensity of the color can be measured to quantitatively or semi-quantitatively determine the urine volume and/or the USG. Nevertheless, while quantitative testing can be performed, qualitative testing is typically employed to provide early testing and monitoring of a health condition. Thus, when a certain urine volume and/or USG is detected, the user or caregiver is given an indication that further quantitative testing can be undertaken. For example, a diaper having an integrated assay device can be periodically used with infants or non-ambulatory patients as part of a monitoring program that tests for urine volume and/or USG. Upon indication of a sufficiently low urine volume and/or high USG, further quantitative testing can then be undertaken to determine the scope and stage of the problem detected so a to provide additional treatment information.

The present disclosure can be better understood with reference to the following examples.

EXAMPLE

Example 1

Figure 4:
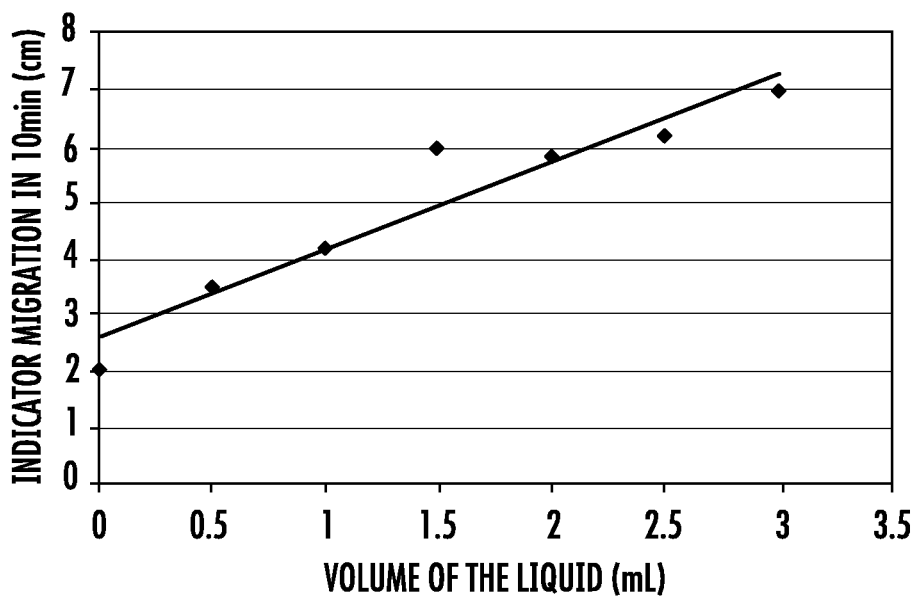
FIG. 4 shows a perspective view of one embodiment of a device that can be used in the present disclosure.

Seven wells were provided that each contained a known amount of liquid and an indicator. Strips of superabsorbent material obtained from a Huggies® diaper where placed in each well for 10 minutes to allow the indicator to migrate along each strip. The distance migrated by the indicator along each strip was measured and plotted against the volume of the liquid in each well as shown in FIG. 4. The plot provides that the distance traveled by the indicator along each strip in each well correlates to the volume of urine insulting each respective test strip.

Example 2

The center of a cellulose paper strip was laminated with a nitrite testing pad removed from urinalysis dipsticks (obtained from Roche) using Scotch tape to make a lateral flow device. To each of five wells on a microtiter plate was added 200 µl of aqueous solution containing different concentrations of sodium chloride, ranging from 0, 25, 50, 100, 150 mg/ml. One end of the lateral flow device was inserted into each well and the aqueous solution was observed to migrate along the device to the other end. 10 minutes later, the nitrite test pad was saturated and presented different colors, ranging from blue, light blue, yellowish blue, bluish yellow and yellow, respectively.

In the interests of brevity and conciseness, any ranges of values set forth in this specification are to be construed as written description support for claims reciting any sub-ranges having endpoints which are whole number values within the specified range in question. By way of a hypothetical illustrative example, a disclosure in this specification of a range of 1-5 shall be considered to support claims to any of the following sub-ranges: 1-4; 1-3; 1-2; 2-5; 2-4; 2-3; 3-5; 3-4; and 4-5.

These and other modifications and variations to the present disclosure can be practiced by those of ordinary skill in the art, without departing from the spirit and scope of the present disclosure, which is more particularly set forth in the appended claims. In addition, it should be understood that aspects of the various embodiments can be interchanged both in whole or in part. Furthermore, those of ordinary skill in the art will appreciate that the foregoing description is by way of example only, and is not intended to limit the disclosure so further described in such appended claims.

What is claimed is:

1. A method for quantitatively or semi-quantitatively determining the volume of test sample of urine, the method comprising:
    contacting the test sample with a fluidic medium of a lateral flow device, the fluidic medium comprising a volume indicator disposed thereon;
    determining the volume of urine in the test sample based on the distance traveled by the volume indicator along the fluidic medium, the distance traveled by the volume indicator corresponding to the volume of urine in the test sample.

2. The method of claim 1, wherein the volume indicator comprises a luminescent compound, a radioactive compound, a colored dye, a metallic substance, liposomes containing signal-producing substances, or combinations thereof.

3. The method of claim 1, wherein the fluidic medium further comprises a polyelectrolyte and a pH indicator disposed thereon, the polyelectrolyte capable of an ion-exchange with the urine so as to add hydrogen ions into the urine, the pH indicator capable of producing a signal corresponding to the hydrogen ion concentration in the urine.

4. The method of claim 3, further comprising determining the ionic strength of the urine based on the signal produced by the pH indicator.

5. The method of claim 3, wherein the polyelectrolyte comprises poly(acrylic acid), poly(maleic acid), maleic acid vinyl methyl ether copolymer, poly(methacrylic acid), styrenemaleic acid copolymer, maleic anhydride/methylvinylether copolymer, poly(vinylamine), poly(4-vinylpyridine), or combinations thereof.

6. The method of claim 3, wherein the pH indicator comprises bromothymol blue, thymol blue, phenol red, neutral red, bromophenol blue, methyl orange, alizarine yellow R, or combinations thereof.

7. A method for quantitatively or semi-quantitatively determining the volume and ionic strength of a test sample of urine, the method comprising:
    providing a lateral flow device comprising a fluidic medium, the fluidic medium having a volume indicator, a polyelectrolyte, and a pH indicator disposed thereon, the polyelectrolyte capable of an ion-exchange with the urine so as to add hydrogen ions into the urine, the pH indicator capable of producing a signal corresponding to the hydrogen ion concentration in the urine;
    contacting the test sample with the fluidic medium of the lateral flow device,
    determining the volume of urine in the test sample based on the distance traveled by the volume indicator along the fluidic medium, the distance traveled by the volume indicator corresponding to the volume of urine in the test sample; and
    determining the ionic strength of the urine based on the signal produced by the pH indicator.

8. The method of claim 7, wherein the volume indicator comprises a luminescent compound, a radioactive compound, a colored dye, a metallic substance, liposomes containing signal-producing substances, or combinations thereof.

9. The method of claim 7, wherein the polyelectrolyte comprises poly(acrylic acid), poly(maleic acid), maleic acid vinyl methyl ether copolymer, poly(methacrylic acid), styrenemaleic acid copolymer, maleic anhydride/methylvinylether copolymer, poly(vinylamine), poly(4-vinylpyridine), or combinations thereof.

10. The method of claim 7, wherein the pH indicator comprises bromothymol blue, thymol blue, phenol red, neutral red, bromophenol blue, methyl orange, alizarine yellow R, or combinations thereof.

11. The method of claim 7, wherein the polyelectrolyte is located upstream from the pH indicator.

12. The method of claim 7, further comprising a sampling zone, the sampling zone configured to receive the test sample of urine.

13. The method of claim 12, wherein the volume indicator is located in the sampling zone and is upstream from the pH indicator.

14. The method of claim 12, wherein the polyelectrolyte is located in the sampling zone and is upstream from the pH indicator.

15. The method of claim 7, further comprising determining the specific gravity of the urine based on the ionic strength.

16. A lateral flow assay device for determining the volume and ionic strength of a test sample of urine, the device comprising a chromatographic medium, the chromatographic medium having a volume indicator, a polyelectrolyte, and a pH indicator disposed thereon;
the volume indicator capable of traveling a distance along the medium that corresponds to the volume of urine in the test sample;
the polyelectrolyte capable of an ion-exchange with the urine so as to add hydrogen ions into the urine; and
the pH indicator capable of producing a signal corresponding to the hydrogen ion concentration in the urine.

17. The lateral flow assay device of claim 16, wherein the volume indicator comprises a luminescent compound, a radioactive compound, a colored dye, a metallic substance, liposomes containing signal-producing substances, or combinations thereof.

18. The lateral flow assay device of claim 16, wherein the polyelectrolyte comprises poly(acrylic acid), poly(maleic acid), maleic acid vinyl methyl ether copolymer, poly(methacrylic acid), styrenemaleic acid copolymer, maleic anhydride/methylvinylether copolymer, poly(vinylamine), poly(4-vinylpyridine) or combinations thereof.

19. The lateral flow assay device of claim 16, wherein the pH indicator comprises bromothymol blue, thymol blue, phenol red, neutral red, bromophenol blue, methyl orange, alizarine yellow R, or combinations thereof.

20. The lateral flow assay device of claim 16, wherein the volume indicator is located upstream from the polyelectrolyte and the pH indicator.

21. An absorbent article capable of determining the ionic strength of urine comprising:
a substantially liquid impermeable layer;
a liquid permeable layer;
an absorbent core positioned between the substantially liquid impermeable layer and the liquid permeable layer; and
a lateral flow assay device integrated into the article and positioned such that the device is in fluid communication with the urine when provided by a wearer of the article, the device comprising:
a chromatographic medium, the chromatographic medium having a volume indicator, a polyelectrolyte, and a pH indicator disposed thereon;
the volume indicator capable of traveling a distance along the medium that corresponds to the volume of urine in the test sample;
the polyelectrolyte capable of an ion-exchange with the urine so as to add hydrogen ions into the urine; and
the pH indicator capable of producing a signal corresponding to the hydrogen ion concentration in the urine.

22. The absorbent article of claim 21, wherein the polyelectrolyte comprises poly(acrylic acid), poly(maleic acid), maleic acid vinyl methyl ether copolymer, poly(methacrylic acid), styrenemaleic acid copolymer, maleic anhydride/methylvinylether copolymer, poly(vinylamine) or poly(4-vinylpyridine).

23. The absorbent article of claim 21, wherein the volume indicator comprises a luminescent compound, a radioactive compound, a colored dye, a metallic substance, liposomes containing signal-producing substances, or combinations thereof.

24. The absorbent article of claim 21, wherein the pH indicator comprises bromothymol blue, thymol blue, phenol red, neutral red, bromophenol blue, methyl orange, or alizarine yellow R.

25. The absorbent article of claim 21, wherein the absorbent article defines a window through which the lateral flow assay device is observable.

* * * * *